(12) United States Patent
Nilsson et al.

(10) Patent No.: US 6,712,508 B2
(45) Date of Patent: Mar. 30, 2004

(54) RADIATION RECORDING DEVICE

(75) Inventors: Börje Nilsson, Uppsala (SE); Jürgen Arndt, Färentuna (SE)

(73) Assignee: Elekta AB (publ), Stockholm (SE)

( * ) Notice: Subject to any disclaimer, the term of this patent is extended or adjusted under 35 U.S.C. 154(b) by 32 days.

(21) Appl. No.: 10/166,260

(22) Filed: Jun. 11, 2002

(65) Prior Publication Data

US 2003/0004503 A1 Jan. 2, 2003

(30) Foreign Application Priority Data

Jun. 11, 2001 (SE) ................................ 0102038

(51) Int. Cl.$^7$ ................................ A61B 6/08
(52) U.S. Cl. ............... 378/205; 378/207; 378/65; 378/18
(58) Field of Search ............... 378/205, 207, 378/65, 18

(56) References Cited

U.S. PATENT DOCUMENTS

| | | | |
|---|---|---|---|
| 3,700,894 A | * | 10/1972 | Counsell ............... 250/50 |
| 3,867,638 A | * | 2/1975 | Golden ............... 250/505 |
| 4,780,898 A | | 10/1988 | Sundqvist |
| 4,818,943 A | * | 4/1989 | Chandra ............... 324/318 |
| 5,116,344 A | | 5/1992 | Sundqvist |
| 5,511,107 A | | 4/1996 | Sliski |
| 5,528,651 A | | 6/1996 | Leksell et al. |
| 5,623,139 A | | 4/1997 | Sliski |
| 5,754,622 A | * | 5/1998 | Hughes ............... 378/65 |

FOREIGN PATENT DOCUMENTS

| | | |
|---|---|---|
| WO | WO 00/29871 | 5/2000 |
| WO | WO 01/10299 | 2/2001 |

* cited by examiner

Primary Examiner—Craig E. Church
Assistant Examiner—Jurie Yun
(74) Attorney, Agent, or Firm—Burns, Doane, Swecker & Mathis, L.L.P.

(57) ABSTRACT

A device is provided for recording in at least two planes radiation from a radiotherapy apparatus. The device comprises a dimensionally stable frame which is adapted to be arranged in a defined position relative to the radiotherapy apparatus, an attachment on the frame for a recording means, and a recording means which extends from the attachment at an acute angle to the frame along an axis of rotation and to the center of the frame. The recording means is adapted to assume at least two defined rotational positions on the axis. In addition, the recording means exhibits a surface for supporting a radiation recording unit, which surface is located in a plane that forms an acute angle with the axis of rotation, the plane of the surface when rotating the recording means being adapted to turn on a single pivot point which is fixed relative to the frame.

20 Claims, 3 Drawing Sheets

Figure 1:
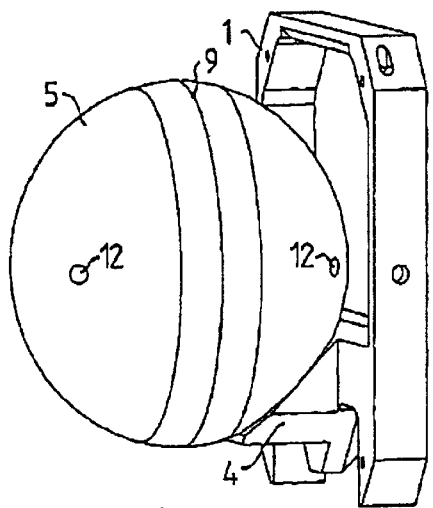

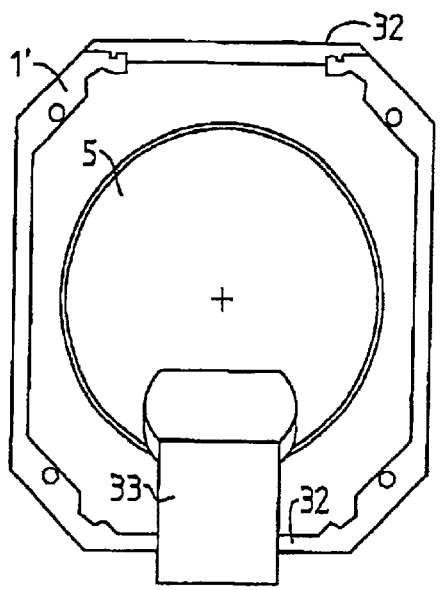
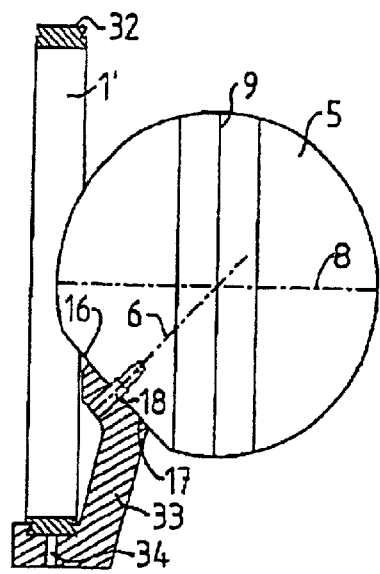
FIG 12
FIG 13
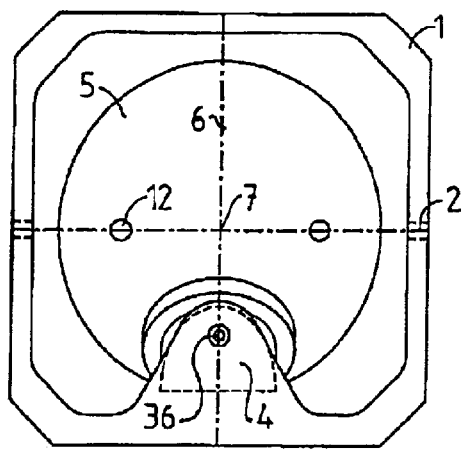
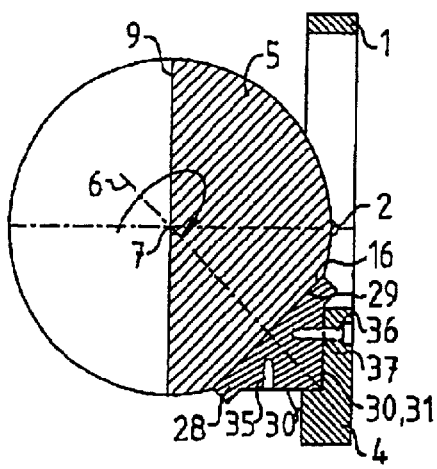
FIG 14
FIG 15
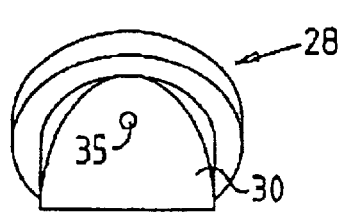
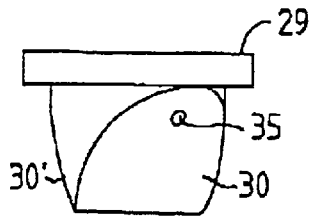
FIG 16
FIG 17

RADIATION RECORDING DEVICE

The present invention relates to a device for recording in at least two planes radiation from a radiotherapy apparatus in a limited area at which the radiation is directed.

In particular, the invention relates to a device for determining the resulting radiation, which from a number of different directions hits a plane or a volume, by recording the radiation on media sensitive to radiation, such as films, semiconductors, ionization chambers, etc., in defined positions and simultaneously or later evaluating recorded radiation data with respect to the distribution of the radiation in time and space by means of a read-out device. The device is especially suited for accurate spatial determination relative to given references of geometrically defined radiation distributions.

The device is also suited for quality assurance of a whole precision radiation procedure by allowing target volumes to be simulated, which volumes can be determined as regards shape and position by medical, image-creating equipment, such as magnetic resonance imaging, computer tomography, etc., for planning treatment of precision radiation and for verifying radiation based on planning.

Furthermore, the device is above all intended to be used together with ELEKTA AB's gamma knife which is presented in the leaflet "Leksell Gamma Knife, Model C, System Description with Technical Overview", cf. U.S. Pat. Nos. 4,780,898 and 5,528,651. Here Leksell Gamma Plan® is advantageously used.

U.S. Pat. No. 5,511,107 discloses what is referred to as a phantom assembly for measuring radiation dose distributions in order to verify the radiation dose applied in a target area. The phantom assembly is constructed of material that is the radiological equivalent of the part of a patient's body that is to be treated, in the presented embodiment the patient's skull. A radiation sensitive film is inserted into a slit in the phantom assembly, a treatment dose is applied to the phantom and the film is analyzed with respect to the radiation exposure. In one embodiment of the phantom, three films have been inserted into one another in three mutually orthogonal planes (in the X, Y and Z directions) and then eight partial cubes have been applied around the films, one in each quadrant, so that a large cube which encloses the films is formed. The partial cubes are kept together by an enclosing casing. The partial cubes are to a certain extent movable in relation to one another, thereby affecting the precision in the positioning of the films and thus the determination of the target area. In addition, the radiation dose cannot be measured in the center of the phantom (the area with the common intersection point of the films (origin)), the center usually being the most interesting area.

The international patent application PCT/CA99/01070 (WO 00/29871) discloses a phantom with films for stereotactic dosemetry. The phantom contains a cassettebox with a plurality of films which are positioned parallel to one another and are separated by distance means of a material which in terms of radiation is similar to the part of the patient's body that is to be treated. The phantom is rotatable about an axis to which all films are parallel. Thus, the plane of the films cannot be made to assume different angles relative to the attachment of the phantom so that a defined center plane of the phantom moves around a fixed center point in the phantom between a position parallel to the attachment and a position perpendicular to the attachment, which is necessary to be able to accurately determine the radiation in a three-dimensional area.

The object of the invention is to provide a device by means of which the common point (iso center) at which the radiation is directed from different directions, is determined with high geometric precision in connection with radiation.

Another object of the invention is to provide a device by means of which the geometrical radiation dose distribution in a radiotherapy apparatus can be determined.

Yet another object of the invention is to provide a device by means of which the total radiation dose can be measured during a simulated treatment process.

According to the invention, these objects are achieved by means of a device as stated by way of introduction, which is characterized in that the device comprises a dimensionally stable frame which is adapted to be arranged in a defined position relative to said radiation sources, an attachment on the frame for a recording means, and a recording means which extends from the attachment at an acute angle to the frame along an axis of rotation and to the center of the frame and which is adapted to assume at least two defined rotational positions on said axis, that the recording means exhibits a surface for supporting a radiation recording unit, which surface is located in a plane that forms an acute angle with said axis of rotation, and that the plane of the surface when rotating the recording means is adapted to turn on a single pivot point which is fixed relative to the frame.

Further developments of the invention are evident from the features stated in the subclaims.

Figure 2:
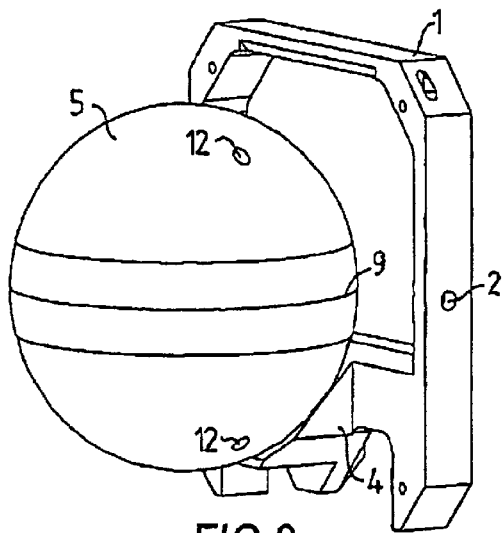
Figure 3:
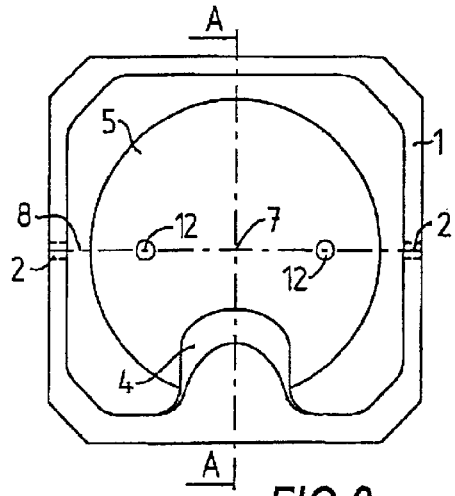
Figure 4:
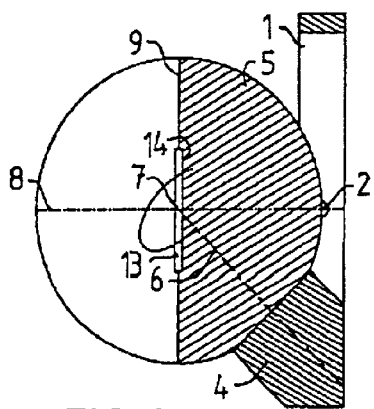
Figure 5:
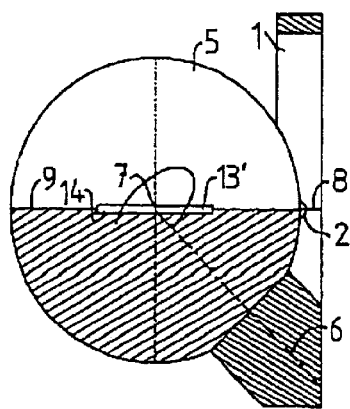
Figure 6:
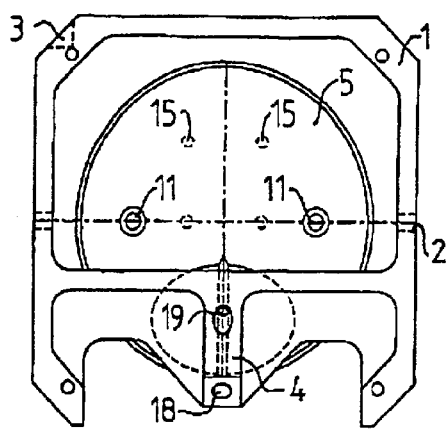
Figure 7:
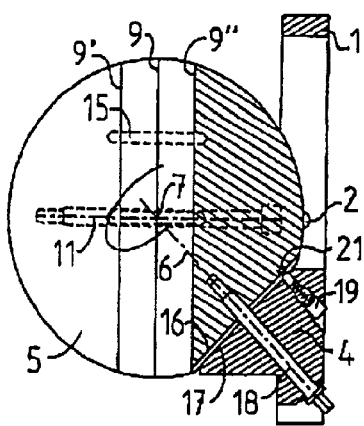
Figure 8:
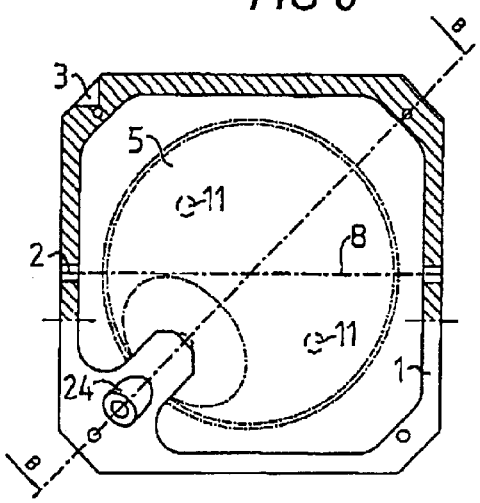
Figure 9:
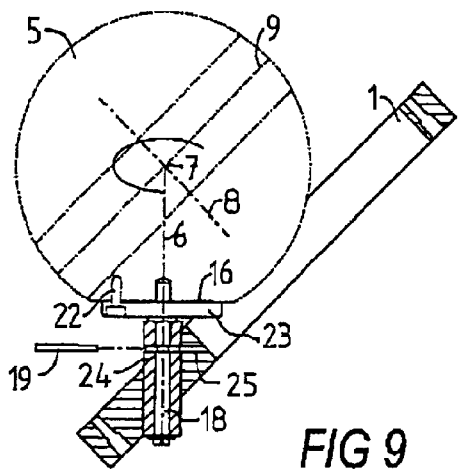
Figure 10:
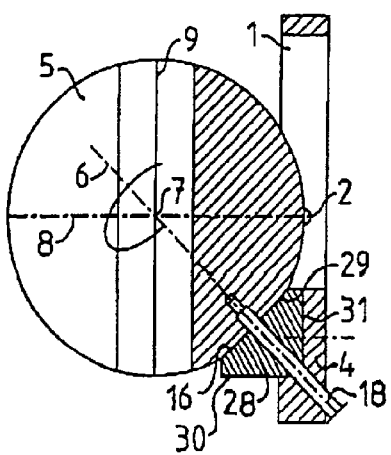
Figure 11:
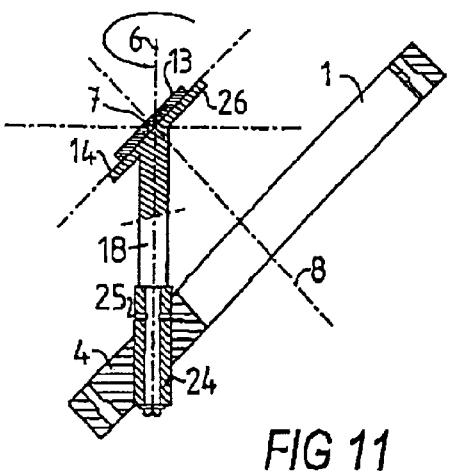

Preferred embodiments of the invention will now be described by way of example and with reference to the accompanying drawings, in which FIGS. 1 and 2 are perspective views from one side of the device according to the invention with the radiation recording unit positioned parallel to the frame of the device and perpendicular to the frame of the device, respectively, the perspective views schematically showing the principle of the invention, FIG. 3 shows a modification of the device in a view from below relative to the views in FIGS 1 and 2, FIG. 4 is a cross-sectional view of the device according to FIG. 3 along the line A—A in a position which corresponds to that in FIG. 1, FIG. 5 shows, in the same view as in FIG. 4, the device according to FIG. 3 in a position which corresponds to that in FIG. 2, FIG. 6 shows, in a view corresponding to that in FIG. 3, a preferred embodiment of the device according to the invention, FIG. 7 shows the embodiment according to FIG. 6 in a view corresponding to that in FIG. 4, FIG. 8 shows, in a part-sectional view corresponding to that in FIG. 3, an alternative embodiment of the device according to FIG. 6, FIG. 9 is a cross-sectional view of the device according to FIG. 8 along the line B—B in a position corresponding to that in FIG. 4, FIG. 10 shows, in a view corresponding to that in FIG. 4, a further embodiment of the device according to the invention, FIG. 11 shows, in a view corresponding to that in FIG. 9, yet another embodiment of the invention which is particularly suited for calibrating a radiotherapy apparatus, FIG. 12 shows, in a top view, i.e. a view opposite to that in FIG. 3, a variant of the device according to the invention, FIG. 13 shows the device according to FIG. 12 in a view opposite to that in FIG. 4, FIG. 14 shows, in a view corresponding to that in FIG. 3, yet another variant of the device according to the invention, FIG. 15 shows the device according to FIG. 14 in a view corresponding to that in FIG. 4, FIG. 16 is a perspective view of the connecting means which is incorporated in the device according to FIGS. 14 and 15, and FIG. 17 is a side view of the connecting means in FIG. 16.

With reference first to FIGS. 1–5 which schematically illustrate the invention, the device according to the invention comprises a dimensionally stable frame 1 with mounting elements in order to detachably mount the device by means of the frame 1 in a medical radiation machine or a radiotherapy apparatus, such as a gamma knife, an apparatus for computer or magnetic tomography, or the like. However, the device will be presented in connection with a gamma knife and, in particular, ELEKTA AD's gamma knife, U.S. Pat. No. 4,780,898, and the associated APS system, U.S. Pat. No. 5,528,651, which are herewith incorporated by reference. The illustrated frame 1 thus comprises mounting elements in the form of a pair of through holes 2 which are centered relative to one another for mounting the frame 1 in a laser knife in the same way as the frame (5) is mounted in the above-mentioned U.S. Pat. No. 5,528,651 (FIGS. 5 and 6). The frame 1 also comprises a recess 3 for positioning the frame in said APS system.

In addition, the frame 1 comprises an attachment 4 which is preferably formed in one piece with the frame. A recording means 5 is movably supported on the attachment and is rotatably arranged on an axis of rotation 6, which will be explained in more detail below. The axis of rotation 6 extends at an acute angle, preferably 45°, to the plane of the frame 1 and through a pivot point 7 approximately in the middle of the frame and in a plane a having said mounting holes 2 but at a distance therefrom. The plane 9 is perpendicular to the plane of the frame, cf. FIG. 5.

In the shown embodiments of the device according to the invention (but not in FIG. 11), the recording means 5 is illustrated in the form of a so-called spherical phantom. A phantom is the name of a dummy which replaces a real head (including bones and brain tissue) in connection with check and reference measurements of radiation focus position, extension and intensity. The obtained measuring data is then used when calculating patient doses, where (also) the patient's head is defined as a spherically shaped water volume (body) with a diameter of 160 mm. A certain degree of compensation for patient specific deviations in size from anatomic or data diagnostic examinations (geometries) may be carried out by software. In the practical routine work, instead of a water phantom, a ditto homogeneous, spherical plastic ball is used, having a density near water. It is often made divisible so that measurements can be carried out in planes near focus. The recording means 5 thus consists of two hemispheres, one of which is filled with parallel lines and the other empty in FIGS. 4 and 5. The parting plane of the sphere or the boundary surfaces 9 of the hemispheres runs/run through the center of the sphere and the axis of rotation 6 cuts the parting plane 9 at a point which coincides with the above-mentioned pivot point 7. The angle between the parting plane 9 and the axis of rotation 6 is acute and, preferably, 45°. The two hemispheres are kept together by clamping means, for example, by bolted joints 11 (see FIG. 7) which extend in associated, through holes 12 in the two hemispheres at a large distance from the pivot point 7.

A radiation recording unit 13 is arranged at and along the parting plane 9, resting against a support surface 14 in a recess in one or both hemispheres, see FIGS. 4 and 5. For reasons of clarity, the unit 13 is not shown in the other Figures except for FIG. 11 in which the unit 13 is not placed in a recess for reasons which are made evident in the description of this embodiment of the device. The radiation recording unit 13 is in the shown embodiments a radiation sensitive film but can, if desirable, be a ionization chamber, a semiconductor detector, a dosimeter or the like, which all are well known to those skilled in the art. Said film is blackened to various degrees depending on how much radiation it has been exposed to, and by means of a scanning device which is connected to a computer (not shown), the radiation doses can at each point of the film be calculated; this too is prior-art technique.

The radiation recording unit or the film 13 is positioned in said recess by means of a pair of pins 15 which extend through the recess and perpendicular to the parting plane, see FIGS. 6 and 7, and which have different dimensions and are arranged at different distances from said pivot point 7. Corresponding holes are punched in the film 13 (not shown but easily understood by those skilled in the art) and owing to the different dimensions and the location of the holes the exposed film cannot be incorrectly positioned in the above-mentioned scanning device. In some known, similar devices, an orientation pin is instead placed in the center of the phantom, which may damage the center area that in most cases is the most interesting measurement area.

In order to be able to determine with high precision said radiation focus position, the geometrical dose distribution and/or the dose distribution in time (power) or the total dose, the recording means is also rotatably arranged on the axis of rotation 6 so that the parting plane 9 (and thus the unit 13) can assume at least two different angular positions relative to the frame 1, and in each angular position, the parting plane 9 runs through the pivot point 7. The parting plane 9 thus carries out a controlled wobbling/pivoting motion along a closed path in three dimensions and with a center of the motion in the pivot point 7 Preferably, the parting plane 9 assumes a position in a first rotational position of the recording means 5 on the axis of rotation 6 which is perpendicular to the position of the parting plane 9 in a second rotational position of the recording means on the axis of rotation, cf. FIGS. 4 and 5. It is also preferred, but not necessary, that the parting plane 9 in one position be parallel to the plane of the frame 1 and in another position is perpendicular to the plane of the frame. By means of the device according to the invention, it is thus very simple to position with high precision the radiation recording unit 13 in different angular positions on a fixed pivot point 7. When the radiation recording unit 13 has been exposed to radiation in one position, for example according to FIG. 4, the unit is removed by the hemispheres being separated and a new unit 13' being mounted. Subsequently, the recording means 5 is rotated so that the unit can be exposed in another position, for example according to FIG. 5, and then also the second unit 13' is removed. With the above-mentioned angle between the axis of rotation 6 and the plane of the frame 1, i.e. 45°, and the indicated angle between the axis of rotation 6 and the parting plane 9, i.e. 45°, the rotation of the recording means 5 in this case thus becomes 180°. By means of the units 13 and 13', the above-mentioned determinations or measurements are then carried out.

By means of a conventional radiation recording device, the measurement takes place in the following manner.

First the phantom is disassembled, the film placed between the hemispheres and the phantom reassembled. The phantom is then accurately oriented in the patient frame and is fastened. The patient frame is then attached in the machine and the film is exposed to rays for a first measurement. Then the patient frame is removed from the machine, the phantom is detached and the film is changed. The phantom then has to be accurately oriented again and be attached to the patient frame with the film plane preferably rotated through 90° to the plane of the film in the first measurement. The patient frame is attached in the machine and a second measurement is carried out. Finally, the patient frame is removed from the machine, the film is developed and the dose distribution is calculated.

As medical radiation equipment is developed to be controlled more precisely, correspondingly higher demands are placed on the equipment for calibration and verification measurements. One problem of the prior-art measuring equipment is to fulfill such higher demands.

One source of failure is that the center of the phantom must have exactly the same position on the two radiation occasions. It is also important that the angle between the plane of the film in the first position and that in the second position can be determined very accurately, As the essential structure and function of the device according to the invention have been described above, reference is now made to FIGS. 6–17 for describing different embodiments of the same.

Reference is first made to FIGS. 6 and 7, which show a first preferred embodiment of the device according to the invention. The recording means 5 exhibits a surface portion 16 which is oriented perpendicular to the axis of rotation 6 and which preferably is in sliding engagement with a supporting surface 17 facing away from the attachment 4 and facing the pivot point 7, and also being oriented perpendicular to the axis of rotation 6. A shaft unit 18 which extends along the axis of rotation 6 is fixedly attached to the recording means (phantom) 5 and is rotatably mounted in the attachment 4, the means 5 being rotatable on the axis of rotation 6. In order to define two or more rotational positions of the means 5 and thus of the radiation recording unit 13, a locking means 19 is arranged in the attachment 4. The locking means 19 can be made to protrude from the supporting surface 17 for locking engagement with two or more associated cavities 21 in the surface portion 16 of the recording means 5, i.e. a cavity 21 for each rotational position The locking means 19 is in FIG. 7 shown as a spring-loaded body but can be a bolt, a cotter pin or the like, which per se is previously known. In addition, these Figures show the above-mentioned clamping means 11 and the positioning pins 15 for the radiation recording unit. FIG. 7 also shows that the phantom 5 can be divisible into more than two portions. There are therefore one, two or more parting planes 9', 9" which are parallel to the parting plane 9 and in which further radiation recording units (not shown) can be mounted in the same manner as described above in connection with the unit 13 and by means of the same through pins 15.

FIGS. 8 and 9 show an alternative construction of the above-mentioned preferred embodiment of the device according to the invention. They also illustrate that the attachment 4 can be arranged in a corner of the frame 1 instead of in a position between two corners of the frame as shown in FIGS. 1–7. In this embodiment, the surface portion 16 of the recording means 5 is supported by and by bolts 22 attached to a disc-shaped element 23 which is oriented perpendicular to the axis of rotation 6 and which preferably is formed in one piece with the shaft unit 18. The shaft unit is rotatably mounted in a sleeve 24 which is fixedly attached to the attachment 4 and the center axis of which coincides with said axis of rotation 6. In this embodiment of the invention, at least one through hole or bore 25 is drilled in the sleeve 24 and in the shaft unit 18 essentially transversely to the axis of rotation 6. The through bores 25 are centered on a common center axis, along which a locking means 19 can be inserted for locking engagement between the sleeve 24 (attachment 4) and the shaft unit 18 as indicated in FIG. 9, which defines two rotational positions of the shaft unit 18 and, thus, of the phantom 5 which are separated by 180°. As discussed above, these rotational positions result in two different orientations of the parting plane 9 and, thus, of the radiation recording unit 13, which are perpendicular to one another if the axis of rotation 6 is arranged at 45° to the plane of the frame 1 and to the parting plane 9. Naturally, the sleeve 24 and the shaft unit 18 can also be provided with more than one pair of co-operating bores 25 in order to provide more possibilities of orientation for the unit 13, in which case they are displaced relative to one another in the direction of the axis of rotation 6.

FIG. 11 illustrates a variant of the embodiment according to FIGS. 8 and 9, which is especially adapted to calibration of a radiotherapy apparatus. What distinguishes these embodiments from one another is above all that the phantom 5 in this embodiment has been replaced with a supporting plate 26, the upper surface 14 of which, i.e. its surface facing away from the frame 1, is adapted to support a radiation recording unit 13 and is positioned at and along said (virtual) parting plane 9. The supporting plate 26 is fixedly attached to, or preferably formed in one piece with, the shaft unit 18.

In the above-discussed embodiments of the invention, the recording means 5 is rotatable on the axis of rotation 6 between at least two fixed angular positions relative to the frame 1, which angular positions are determined by the locking means 19 in co-operation with the cavity 21 and the bore 25, respectively. However, an automatic, two-dimensional radiation measuring can also be made in all planes in the target area about the pivot point 7 by making the shaft unit 18 rotate, for example by means of a motor which is attached to the frame 1 and which in a per se known manner drives the shaft unit 18 (not shown) The shaft unit is thus rotatably mounted directly in the attachment 4 of the frame 1 (see FIGS. 7 and 10) or, preferably, indirectly in the attachment 4 by being supported in the sleeve 24 (see FIG. 11). The radiation measuring is based on the fact that the angle of rotation of the shaft unit 18 is always known and the radiation recording unit 13 is a continuously recording detector which is preferably positioned as the unit 13 in FIG. 11.

With reference to FIG. 10, a further embodiment is shown. In this embodiment, a cone-shaped connecting means 28 is with its base 29 fixedly attached to the surface portion 16 of the recording means 5, cf. FIG. 7. The shaft unit 18 presented above is fixedly attached to the connecting means 28 and/or the recording means 5 and is rotatably mounted in the attachment 4. The attachment in this embodiment does not protrude from the frame 1 as in the embodiments mentioned above, but is countersunk in a portion of the frame having a contact surface 31 which as regards its shape corresponds to the circumferential area 30 of the connecting means 28 for sliding engagement between these two, With the aid of a locking means 19 in the attachment 4 which co-operates with cavities 21 (only schematically indicated in FIG. 10) in the same manner as in the embodiment according to FIGS. 6 and 7, the recording means 5, and thus the radiation recording unit 13, can be set in the positions discussed above.

The embodiment according to FIGS. 12 and 13 refers to a common stereotactic frame 1' as the frame shown in U.S. Pat. No. 5,116,344 which is incorporated herewith by reference. The frame (1) is along at least two sides (2 and 3) formed with dovetail-shaped guide means 32 and along one of these, the recording means 5 is displaceably supported by an arm 33 extending towards the inside of the frame 1'. The arm 33 can be fixed in position on the guide means 32 by a screw 34. The recording means 5 is by means of a shaft unit 18 rotatably mounted on the free end of the arm 33 and the parting plane 9 is positioned in the same manner as in the embodiment according to FIGS. 6 and 7.

In the embodiments according to FIGS. 6–13, the recording means 5 is rotatably arranged on the axis of rotation 6 by means of a shaft unit 18 which is rotatably mounted in the attachment 4. However, the recording means or the phantom 5 can also be rotated between fixed positions on the axis of rotation 6 without any help from a shaft unit. One example of this is illustrated in FIGS. 14–17. As in the embodiment according to FIG. 10, a connecting means 28 with its base 29 is fixedly attached to the surface portion 16 of the recording means 5. The connecting means 28 is in this case essentially wedge-shaped and has two supporting surfaces 30, 30' protruding from the recording means 5, which are symmetrically arranged relative to the axis of rotation 6 and are arranged at right angles to one another as is evident from FIG. 15. Moreover, the supporting surfaces 30, 30' each has one threaded hole 35. As in the embodiment according to FIG. 10, the frame 1 has an attachment 4 which is countersunk in a portion of the frame having a plane contact surface 31 and a through bore 36 for a mounting bolt 37.

In order to set the parting plane 9, and thus the recording unit 13, in one position, for example parallel to the frame 1 as illustrated in FIG. 15, one supporting surface 30 of the connecting means is made to abut against the contact surface 31 of the attachment and the recording means 5 is fixed in this position by means of the bolt 37 which via the bore 36 is screwed into the threaded hole 35 in the connecting means 28. When it is desirable to rotate the parting plane 9 through 90°, i.e. in this example perpendicular to the frame 1, the bolt 37 is unscrewed from the hole 35 and the recording means 5 is rotated freely (completely released from the attachment and the frame), after which the second support surface 30' of the connecting means is screwed onto the contact surface 31 of the attachment in the manner indicated above.

In the last-mentioned embodiment of the device according to the invention, the connecting means has been described comprising two symmetrically arranged supporting surfaces 30, 30'. As is easily understood, the connecting means 28 can, however, have three or more supporting surfaces, preferably symmetrically arranged with respect to the axis of rotation 6. Furthermore, the bolt 37 can be placed at an acute angle to the frame 1 instead of perpendicular to the frame, i.e. in the longitudinal direction of the axis of rotation 6, in which case the bolt need not be completely unscrewed from the recording means 5 when changing its rotational position, cf. FIG. 10, where the shaft unit 18 may be replaced with the bolt 37.

In connection with the drawings, different features of the device according to the invention have been presented. Naturally, the features shown in the Figures may be combined/replaced one with the other, if desirable. The attachment can also be arranged in an optional position on the frame on condition that the pivot point is fixed relative to the frame, i,e. that it does not change its position when the parting plane is rotated.

The invention is not limited to that described above and shown in the drawings and can be changed within the scope of the claims.

What is claimed is:

1. A device for recording in at least two planes radiation from a radiotherapy apparatus, in a limited area at which the radiation is directed, wherein the device comprises a dimensionally stable frame (1) which is adapted to be arranged in a defined position relative to said radiotherapy apparatus, an attachment (4) on the frame (1) for a recording means, and a recording means (5) which extends from the attachment (4) at an acute angle to the frame (1) along an axis of rotation (6) and to the center of the frame (1) and which is adapted to assume at least two defined rotational positions on said axis (6), that the recording means (5) exhibits a surface (14) for supporting a radiation recording unit (13), which surface (14) is located in a plane (9) that forms an acute angle with said axis of rotation (6), and that the plane (9) or the surface (14) when rotating the recording means (5) is adapted to turn on a single pivot point (7) which is fixed relative to the frame (1).

2. A device as claimed in claim 1, wherein the recording means (5) comprises a homogeneous body (5) of plastic material which is divided along said plane (9) into two portions which are clamped together by a clamping means (11) and between which the radiation recording unit (13) is fastened.

3. A device as claimed in claim 2, wherein the homogeneous body (5) is divided into at least three portions along planes (9, 9', 9") which are parallel to said plane (9), said portions being clamped together by common clamping means (11).

4. A device as claimed in claim 3, wherein the connecting means (28) is essentially wedge-shaped and has at least two surfaces (30, 301) protruding from the homogeneous body, which are symmetrically arranged relative to the axis of rotation (6) and are arranged at right angles to one another, said surfaces (30, 30') being intended to alternately be fixedly attached to said attachment (4).

5. A device as claimed in claim 3, wherein the homogeneous body has a surface portion (16) which is oriented perpendicular to said axis of rotation (6) and which is in sliding engagement with a supporting surface (17) facing away from said attachment (4) and facing the inside of the frame and being oriented perpendicular to the axis of rotation (6).

6. A device as claimed in claim 5, wherein the homogeneous body has a surface portion (16) which is oriented perpendicular to said axis of rotation (6) and which is in sliding engagement with a supporting surface (17) facing away from said attachment (4) and facing the inside of the frame and being oriented perpendicular to the axis of rotation (6).

7. A device as claimed in claim 3, wherein the homogeneous body has a surface portion (16) which is oriented perpendicular to said axis of rotation (6) and which is in sliding engagement with a supporting surface (17) facing away from said attachment (4) and facing the inside of the frame and being oriented perpendicular to the axis of rotation (6).

8. A device as claimed in claim 2, wherein two pins (15) of different dimensions are arranged in each parting plane (9, 91, 90) and at different distances from the center (7) of the homogeneous body (5), which pins (15) are adapted to be inserted into correspondingly dimensioned holes in the recording unit (13) for positioning thereof in the associated parting plane (9, 9', 9").

9. A device as claimed in claim 8, wherein the homogeneous body has a surface portion (16) which is oriented perpendicular to said axis of rotation (6) and which is in sliding engagement with a supporting surface (17) facing away from said attachment (4) and facing the inside of the frame and being oriented perpendicular to the axis of rotation (6).

10. A device as claimed in claim 2, wherein the homogeneous body has a surface portion (16) which is oriented perpendicular to said axis of rotation (6) and which is in sliding engagement with a supporting surface (17) facing away from said attachment (4) and facing the inside of the frame and being oriented perpendicular to the axis of rotation (6).

11. A device as claimed in claim 10, wherein a locking means (19) is arranged in the attachment (4) and can be made to protrude from said supporting surface (17) at a distance from the shaft unit (18) for locking engagement with corresponding cavities (21) in said surface portion (16) in order to fix the homogeneous body in defined positions on the axis of rotation (6).

12. A device as claimed in claim 2, wherein a connecting means (28) is fixedly attached to the homogeneous body (5) symmetrically on the axis of rotation (6) and in abutment against said attachment (4).

13. A device as claimed in claim 12, wherein the connecting means (28) is essentially wedgeshaped and has at least two surfaces (30, 301) protruding from the homogeneous body, which are symmetrically arranged relative to the axis of rotation (6) and are arranged at right angles to one another, said surfaces (30, 30') being intended to alternately be fixedly attached to said attachment (4).

14. A device as claimed in claim 13, wherein the connecting means (28) is essentially wedge-shaped and has at least two surfaces (30, 301) protruding from the homogeneous body, which are symmetrically arranged relative to the axis of rotation (6) and are arranged at right angles to one another, said surfaces (30, 30') being intended to alternately be fixedly attached to said attachment (4).

15. A device as claimed in claim 1, wherein the recording means (5) comprises a shaft unit (16) which is rotatably mounted in said attachment (4) and which is fixedly connected to said surface (14) for supporting the radiation recording unit (13) and the longitudinal direction of which coincides with said axis of rotation (6).

16. A device as claimed in claim 15, wherein the shaft unit (18) is freely rotatably mounted in the attachment (4), and that the radiation recording unit (13) is a continuously recording detector.

17. A device as claimed in claim 15, wherein at least one locking means (19) is arranged in the attachment (4) and is capable of being brought into locking engagement with a corresponding transverse bore (25) in the shaft unit (18) in order to fix the radiation recording unit (13) in defined positions relative to the axis of rotation (6).

18. A device as claimed in claim 1, wherein said attachment (4) has the shape of an arm (33) which is displaceably attached to the frame (1) and which extends towards the center of the frame.

19. A device as claimed in claim 1, wherein the frame (1) is formed in one plane, that the axis of rotation (6) is oriented at an angle of 45, to the plane of the frame (1), and that each surface (14) with a recording unit (13) is oriented at an angle of 450 to the axis of rotation (6).

20. A device as claimed in claim 1, wherein the frame (1) is a stereotactic frame included in a stereotactic instrument, and that the surface/surfaces (14) of the recording means for supporting a radiation recording unit (13) is/are adapted to be inserted into the treatment space of a radiotherapy apparatus in order to record the radiation in an area of the space.

* * * * *